(12) United States Patent
Pfister (10) Patent No.: US 8,880,153 B2
(45) Date of Patent: Nov. 4, 2014

(54) ANGIOGRAPHY SYSTEM FOR THE ANGIOGRAPHIC EXAMINATION OF A PATIENT AND ANGIOGRAPHIC EXAMINATION METHOD

(75) Inventor: Marcus Pfister, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 175 days.

(21) Appl. No.: 13/421,891

(22) Filed: Mar. 16, 2012

(65) Prior Publication Data
US 2012/0238871 A1    Sep. 20, 2012

(30) Foreign Application Priority Data

Mar. 18, 2011    (DE) .......................... 10 2011 005 777

(51) Int. Cl.
| | |
|---|---|
| *A61B 6/03* | (2006.01) |
| *A61B 6/00* | (2006.01) |
| *G06K 9/00* | (2006.01) |
| *A61B 6/12* | (2006.01) |
| A61B 6/04 | (2006.01) |

(52) U.S. Cl.
CPC .................. *A61B 6/504* (2013.01); *A61B 6/487* (2013.01); *A61B 6/481* (2013.01); *A61B 6/0407* (2013.01); *A61B 6/4441* (2013.01); *A61B 6/12* (2013.01); *A61B 6/5235* (2013.01)
USPC ........... 600/431; 600/407; 600/410; 600/425; 382/130; 382/132; 378/4; 378/19; 378/95

(58) Field of Classification Search
CPC .......... A61B 6/025; A61B 6/03; A61B 6/032; A61B 6/48
USPC .......... 600/407, 410, 425, 431; 382/130, 132; 378/4, 19, 95
See application file for complete search history.

(56) References Cited

U.S. PATENT DOCUMENTS

| | | |
|---|---|---|
| 7,500,784 B2 | 3/2009 | Grebner |
| 2003/0179917 A1 | 9/2003 | Faber |

(Continued)

FOREIGN PATENT DOCUMENTS

| | | |
|---|---|---|
| DE | 10213284 B4 | 11/2007 |
| DE | 102006025917 A1 | 12/2007 |

(Continued)

OTHER PUBLICATIONS

Arnulf Oppelt Imaging Systems for Medical Diagnostics, 2005, pp. 65-66, Publicis Corporate Publishing, Germany; Others.

(Continued)

*Primary Examiner* — Baisakhi Roy (57) ABSTRACT

An angiography system for angiographic examination of a patient is provided. The system has an x-ray emitter and an x-ray image detector attached to the ends of a C-arm, a patient support couch, a system control unit, an image system and a monitor. The system control unit generates a mask image that detects a reference image, effects a registration of the reference image to the C-arm, whereby if necessary a segmentation of the examination object is implemented in the reference image, contrasts image regions lying inside of the segmentation in order to generate a mask image, and subtracts the mask image from fluoroscopy live images acquired by the angiography system without contrast agent in order to form a roadmap image. The image system effects a reproduction of the roadmap images on the monitor.

20 Claims, 9 Drawing Sheets

(56) References Cited

U.S. PATENT DOCUMENTS

| | | |
|---|---|---|
| 2006/0215817 A1* | 9/2006 | Watanabe .................. 378/114 |
| 2007/0003014 A1* | 1/2007 | Boese et al. ................ 378/95 |
| 2008/0080757 A1 | 4/2008 | Scheuering et al. |
| 2008/0101670 A1* | 5/2008 | Baumgart et al. ........... 382/128 |
| 2008/0212857 A1* | 9/2008 | Pfister et al. ............... 382/130 |
| 2009/0067568 A1* | 3/2009 | Hall et al. .................. 378/4 |
| 2009/0092308 A1* | 4/2009 | Deuerling-Zheng et al. . 382/132 |
| 2011/0007956 A1 | 1/2011 | Meyer et al. |
| 2011/0038458 A1 | 2/2011 | Spahn |

FOREIGN PATENT DOCUMENTS

| | | |
|---|---|---|
| DE | 102006046285 A1 | 4/2009 |
| DE | 102008023918 A1 | 11/2009 |
| DE | 102009032059 A1 | 1/2011 |
| DE | 102009037243 A1 | 2/2011 |

OTHER PUBLICATIONS

Product Guide: Guidewires Stent Grafts by Medtronic and Lombard Medical Technologies Cardiology today, Jan. 2011, p. 36,; Others.

* cited by examiner

ANGIOGRAPHY SYSTEM FOR THE ANGIOGRAPHIC EXAMINATION OF A PATIENT AND ANGIOGRAPHIC EXAMINATION METHOD

CROSS REFERENCE TO RELATED APPLICATIONS

This application claims priority of German application No. 10 2011 005 777.3 filed Mar. 18, 2011, which is incorporated by reference herein in its entirety.

FIELD OF INVENTION

The invention relates to an angiography system for the angiographic examination or intervention of an organ, vascular system or other body regions as an examination object of a patient using an x-ray emitter, an x-ray image detector, which are attached to the ends of a C-arm, a patient support couch with a couch plate for supporting the patient, a system control unit, an imaging system and a monitor as well as an angiographic examination method for the angiography system.

BACKGROUND OF INVENTION

An angiography system of this type is known for instance from U.S. Pat. No. 7,500,784 B2 which is explained with the aid of FIG. 1.

Figure 1:
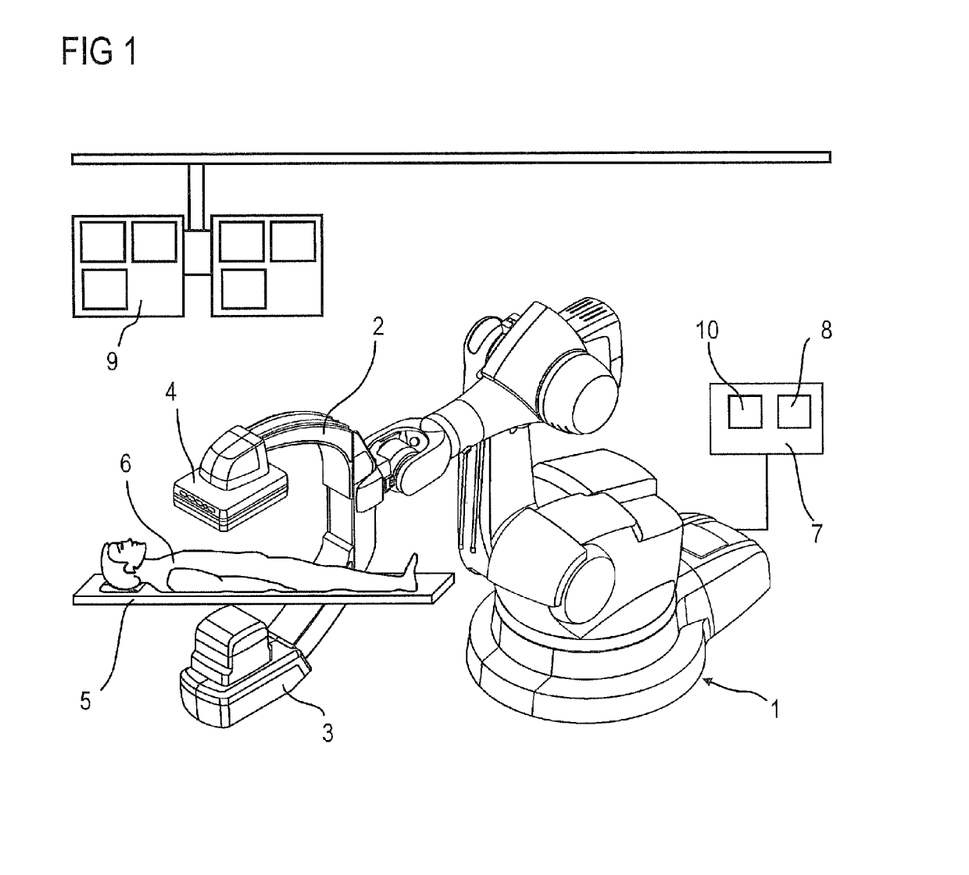
FIG. 1 shows a known C-arm angiography system having a industrial robot as a carrying apparatus.

FIG. 1 shows a monoplanar x-ray system shown as an example having a C-arm 2 held by a stand 1 in the form of a six-axle industrial or articulated arm robot, to the ends of which an x-ray radiation source, for instance an x-ray emitter 3 having x-ray rubes and a collimator, and an x-ray image detector 4 as an image recording unit are attached.

By means of the articulated arm robot known for instance from U.S. Pat. No. 7,500,784 B2, which preferably comprises six axes of rotation and thus six degrees of freedom, the C-arm 2 can be spatially adjusted in any way, for instance by being rotated about a center of rotation between the x-ray emitter 3 and the x-ray image detector 4. The inventive angiographic x-ray system 1 to 4 can in particular be rotated about centers of rotation and axes of rotation in the C-arm plane of the x-ray image detector 4, preferably about the center point of the x-ray image detector 4 and about the axes of rotation which intersect the center point of the x-ray image detector 4.

The known articulated arm robot comprises a base frame, which is fixedly mounted for instance on a floor. A carousel is rotatably fastened thereon about a first axis of rotation. A robot rocker is pivotably attached to the carousel about a second axis of rotation, to which a robot arm is rotatably fastened about a third axis of rotation. A robot hand is rotatably attached to the end of the robot arm about a fourth axis of rotation. The robot hand comprises a fastening element for the C-arm 2, which can be pivoted about a fifth axis of rotation and can be rotated about a sixth axis of rotation which proceeds at right angles thereto.

The realization of the x-ray diagnostics facility is not dependent on the industrial robot. Conventional C-arm devices can also be used.

The x-ray image detector 4 may be a rectangular or square, flat semi-conductor detector, which is preferably created from amorphous silicon (a-Si). Integrated and possibly counting CMOS detectors can however also be used.

A patient 6 to be examined as the examination object is located in the beam path of the x-ray emitter 3 on a couch plate 5 of a patient support couch. A system control unit 7 with an imaging system 8 is connected to the x-ray diagnostics facility, said imaging system receiving and processing the image signals of the x-ray image detector 4 (control elements are not shown for instance). The x-ray images can then be observed on displays of a monitor 9. A known collision calculator 10 is further provided in the system control unit 7, the function of which is described again in more detail.

Figure 2:
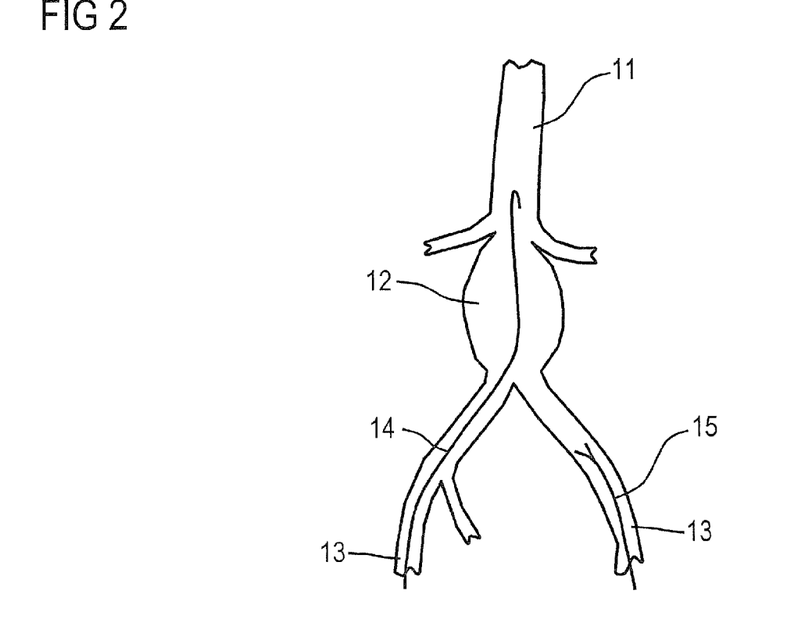
FIG. 2 shows an abdominal aorta with an aortic aneurysm.

Instead of the x-ray system shown by way of example in FIG. 1 having the supporting stand 1 in the fond of the six-axle industrial or articulated arm robot, as shown in simplified form in FIG. 2, the angiographic x-ray system can also comprise a normal ceiling or floor-mounted retaining bracket for the C-arm 2.

Instead of the C-arm 2 shown by way of example, the angiographic x-ray system can also comprise separate ceiling and/or floor-mounted retaining brackets for the x-ray emitter 3 and x-ray image detector 4, which are fixedly electronically coupled for instance.

By means of the articulated arm robot known from the afore-cited U.S. Pat. No. 7,500,784, B2, rotation angiographs, so-called DynaCTs, can be created in order to generate 3D image recordings of an aneurysm for instance.

Angiography systems of this type are used in the field of fluoroscopy-controlled, interventional repairs of abdominal aortic aneurysms.

An abdominal aortic aneurysm (AAA) is an aneurysm on the abdominal aorta. This is treated by inserting a stent graft. Guide wires and catheters are introduced into the aorta by way of the two strips, by way of which one or several stent grafts, otherwise known as composite stent-graft devices, are introduced (see FIG. 3), such as are shown for instance in Cardiology today, January 2011, page 36. The aim when inserting these stent grafts is to position the "landing zone" of the vascular prosthesis as far as possible in the healthy vascular wall, but in the process not to cover any important vessel outlets. The outlets of the renal arteries, the superior mesenteric artery (arteria mesenterica superior), the truncus coeliacus, and the internal pelvic arteries (arteria iliaca interna) are to be kept free. One sensitive point is the disposal of the "main stent" in the aorta, whereby the said vessel outlets are not permitted to be closed. With complex stents which include the leg arteries, the final stent must sometimes be composed of "partial stents" (for instance an aortic stent to which stents for leg arteries are attached).

The so-called "roadmapping" technology is frequently used for the precise positioning of the stents, such as is described again by way of example for instance with the aid of FIGS. 4 to 9. The idea here is provide the physician with a type of "map" to navigate the instrument by continuously displaying the vessels. A mask image is herewith initially generated by administering contrast agent. The subsequently recorded fluoroscopy live images are now captured without contrast agent, nevertheless with an introduced instrument. If the mask image is deduced from the live images, the roadmap images are obtained, on which the anatomical background was "subtracted" and the vessels appear to be light-colored and the introduced instrument appears to be dark. The problem is that a new mask image has to be created for each new angulation.

In order, for monitoring purposes, not to have to inject contrast agent for a constant vessel representation during the complex stent positioning, a reference image can also be correctly anatomically overlaid which shows the vessels, in the case of the aorta and the outgoing vessels. This reference image may either be a 2D angiography (DSA—digital subtraction angiography) or, more expediently, a previously captured 3D image data record, for instance a CT angiography, of the aneurysm. These show more details and can be overlaid at any angulation of the C-arm (see FIGS. 4 to 9). Occasionally such a reference volume or image is also presegmented (see FIGS. 10 and 11).

This representation may however be unfamiliar to the physician. Furthermore, the overlaid reference image may possibly cover important details of the fluoroscopy image.

In summary, common knowledge is:
The manual or automatic segmentation of AAAs and the corresponding calculation of centerlines,
The (flexible) 2D/3D or 3D/3D registration, for instance of 2D and 3D angiographs,
The roadmap technology and
The adaptive 2D reference overlay, such as is described for instance in DE 10 2008 023 918 A1.

SUMMARY OF INVENTION

The invention assumes the object of embodying an angiography system for the angiographic examination of a patient and angiographic examination method for examining the patient of the type cited in the introduction such that mask images of this type are also generated from any angulations without the repeated administration of contrast agents, so that the physician is able to achieve his/her usual roadmap representation.

The object is achieved in accordance with the invention for an angiography system of the type cited in the introduction by the features cited in the independent claim. Advantageous embodiments are specified in the dependent claims.

The object is achieved in accordance with the invention for an angiography system, such that an apparatus for generating a mask image is provided in the system control unit, which is embodied such that, it captures a reference image adapted to different or changed imaging geometries of the angiography system,
it effects a registration of the reference image to the C-arm, whereby a segmentation of the examination object is if necessary implemented in the reference image,
it contrasts image regions lying within the segmentation in order to generate a mask image, and
it subtracts this mask image from fluoroscopy live images acquired by the angiography system without contrast agent to form a roadmap image, and
that the image system effects a reproduction of the roadmap images on the monitor. As a result, a creation of a mask image for a roadmap is achieved without the renewed or repeated administration of contrast agent for changing angulations, couch positions etc.

If pre-interventional, segmented 3D data is used, no segmentation of the examination object needs to be implemented in the reference image. On the other hand, after registering the reference image to the C-arm, the examination object has to be segmented in the reference image.

An adaptive reference image is an anatomically correct overlay (2D/3D), which adjusts to changed imaging geometry (in other words C-arm angle, zoom etc. and/or couch positions). The registration of the reference image to the C-arm is known for instance from "Imaging Systems for Medical Diagnostics", edited by Arnulf Oppelt, 2005, pp. 65-66.

It has proven advantageous if the image regions lying within the segmentation are contrasted such that they are set to black in order to darken or homogenously color a specific offset value according to the local thickness of the vessel. Alternatively, the local thickness of the vessel can be calculated from the distances of the vessel edges detected by means of the segmentation or can be replaced, colored and/or darkened according to a mathematical forward projection of the segmentation (DRR).

The adaptive reference image which is registered to the C-arm may advantageously be a 2D reference image which adjusts to different settings of the angiography system, whereby the different settings may be changes to the zoom, the SID and/or couch settings.

According to the invention, the adaptive reference image which is registered to the C-arm may be a 3D data record of a CT angiography implemented prior to an intervention or a C-arm CT angiography recorded during the intervention.

It has proven advantageous for the apparatus for generating a mask image to effect a display of additional information, whereby this additional information can be displayed through recesses of mask parts.

The additional information may be inventive information relating to vascular courses, vascular occlusions, orifices and/or thrombi.

The object is inventively achieved for an angiographic examination method for examining an organ, vascular system or other body regions of a patient with an afore-cited apparatus by means of the following steps:
S1) Detecting a reference image
S2) Registering the reference image to the C-arm, whereby a segmentation of the examination object is if necessary implemented in the reference image,
S3) Creating a mask image from the reference image for a roadmap image with different alignments of the C-arm, without administering contrast agent,
S4) Creating a mask image from the reference image for a roadmap image with different alignments of the C-arm without administering contrast agent,
S5) Generating fluoroscopy live images,
S6) Subtracting the mask image from the fluoroscopy live images in order to generate roadmap images and
S7) Reproducing the roadmap images.

If pre-interventional 3D data of a computed tomography for instance is used to detect a reference image, these may already be segmented. It is only then that a registration of the reference image to the C-arm takes place. The segmentation can therefore also take place as a first step prior to registration.

If by contrast a 3D data record is created by means of DynaCT, it is only then that a registration of the reference image to the C-arm takes place and then the segmentation of the examination object in the reference image.

The generation of a mask is simplified if in order to create a mask image from the reference image according to step S4, the image regions lying within the segmentation of the aneurysm are contrasted. This may be inventively achieved if they are set to black or they are "darkened" according to the local thickness of the vessel.

An aneurysm of a patient can advantageously be segmented for segmentation purposes according to step 3).

The navigation of instruments is simplified by improved visibility in the vessel, if additional information is displayed in the mask image and/or the roadmap image. These can be displayed in accordance with the invention through recesses of mask parts, whereby the additional information is information relating to vascular courses, vascular occlusions, orifices and/or thrombi.

BRIEF DESCRIPTION OF THE DRAWING

The invention is described in more detail below with the aid of exemplary embodiments shown in the drawing, in which.

DETAILED DESCRIPTION OF INVENTION

An abdominal aorta 11 is shown in FIG. 2, which comprises an abdominal aortic aneurysm (AAA). An abdominal aortic aneurysm (AAA) 12 is an aneurysm on the abdominal aorta 11.

Figure 3:
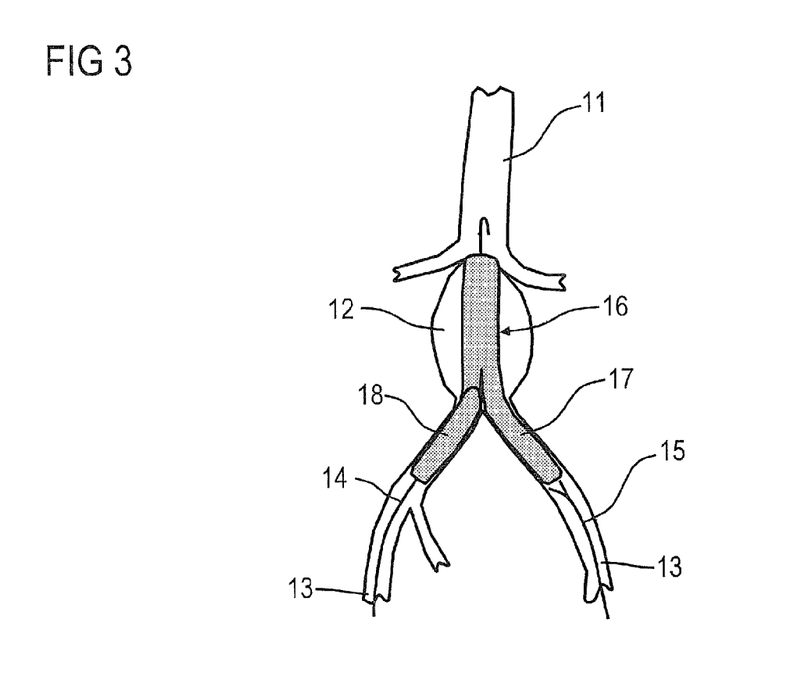
FIG. 3 shows the aorta according to FIG. 2 with an inserted stent graft.

The aortic aneurysm 12 is treated by inserting a stent graft, in other words a composite stent graft device, such as is shown in FIG. 3. To this end, guide wires 14 and catheters 15 are introduced into the aorta 11 by way of the two strips through the leg arteries 13, by way of which the stent grafts 16 are introduced.

With complex stent grafts 16, which include the leg arteries 13, the final stent must sometimes be composed of "partial stents", whereby a partial stent 18 for the other leg artery 13 is "flanged" on an aortic stent 17 for instance, which protrudes through the AAA into one of the leg arteries 13, through a so-called window.

Figure 4:
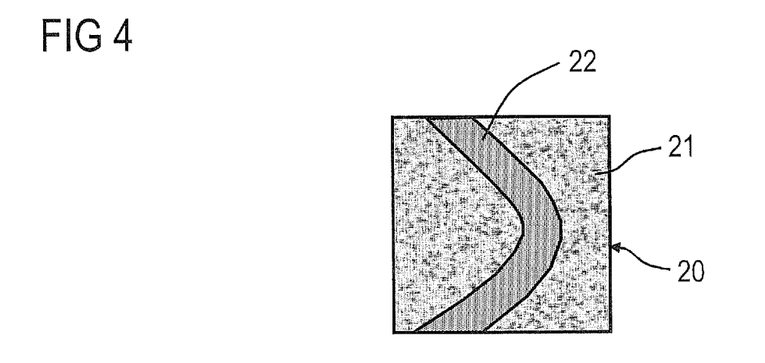
FIGS. 4 to 6 show schematic representations to explain the road mappings.
Figure 5:
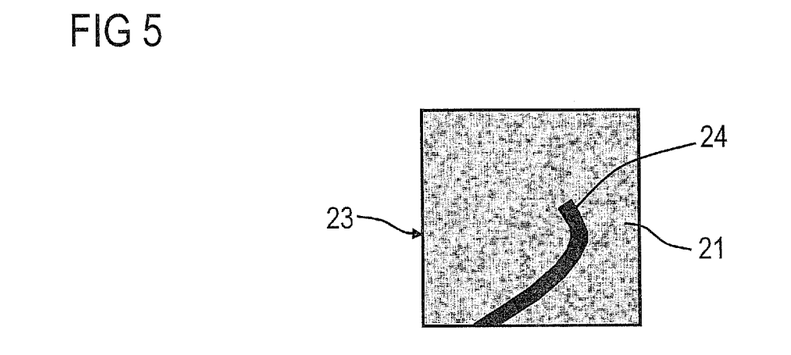
Figure 6:
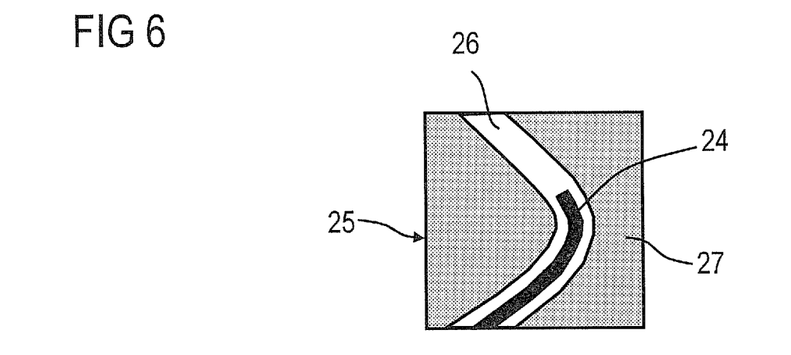

The principle behind road mapping technology is now indicated in FIGS. 4 to 6 with the aid of a schematic representation. The basic idea behind the road mapping technology is to provide the physician with a type of "map" for navigating instruments during the examination and intervention above all in body regions which are subjected to less movement, such as the aorta or the cranium, by constantly displaying the vessels. A mask image 20 (FIG. 4) is herewith initially generated by administering contrast agent, which for instance indicates an anatomical background 21 with a contrast agent-filled aorta 22. Subsequently acquired fluoroscopy live images 23 (FIG. 5) are now recorded without contrast agent but with an introduced instrument 24. If the mask image 20 according to FIG. 4 is taken from these fluoroscopy live images 23, a roadmap image 25 (FIG. 6) is obtained, from which the anatomical background 21 was "subtracted". The vessels 26 appear to be light-colored, the introduced instrument 24 appears to be dark and the subtracted anatomical background 27 appears to be gray.

Figure 7:
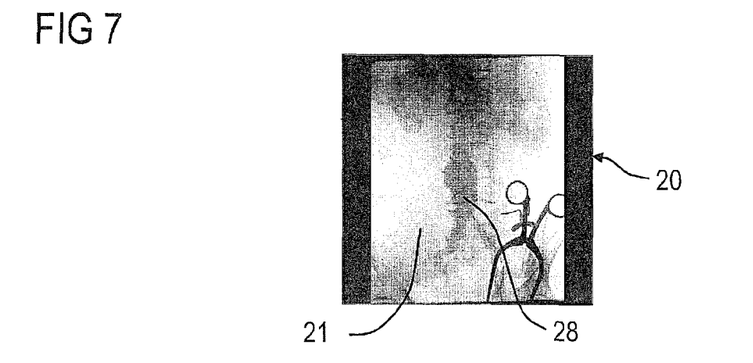
FIGS. 7 to 9 show road mapping as an example of an abdominal aortic aneurysm.
Figure 8:
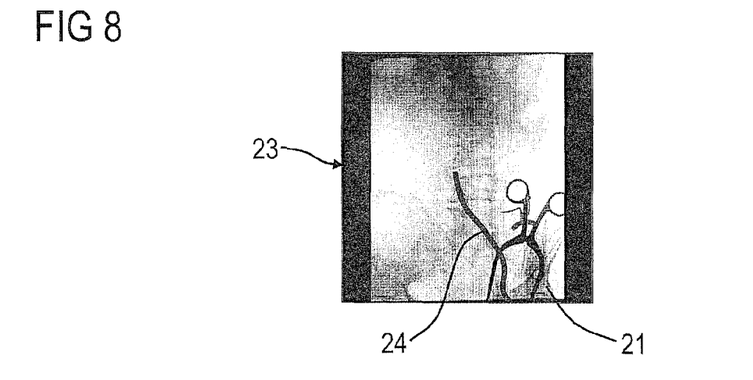
Figure 9:
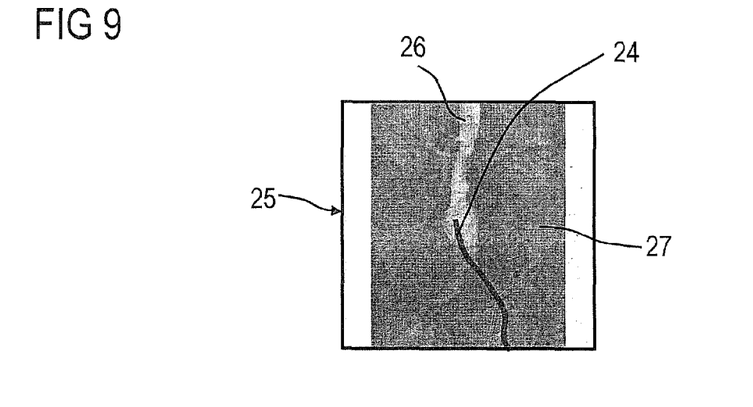

With the aid of FIGS. 7 to 9, the principle behind the road mapping technology according to FIGS. 4 to 6 is now shown in real x-ray images in the example of an aortic aneurysm 28, which can be seen in the mask image 20 (FIG. 7) on account of the contrast agent administration in front of the anatomical background 21. In the subsequently recorded fluoroscopy live images 23 according to FIG. 8, the introduced instrument 24 is now additionally visible; the aortic aneurysm 28 is however only very unclearly visible, if at all, on account of the missing contrast agent.

By subtracting the mask image 20 according to FIG. 7 and these fluoroscopy live images 23 according to FIG. 8, only the roadmap images 25 shown in FIG. 9 are obtained, on which the anatomical background 21 was almost completely eliminated. The vessels 26 formerly filled with contrast agent and the aortic aneurysm 28 appear to be lighter colored than the gray subtracted anatomical background 27 and the reproduced dark instrument 24. The physician is now able to see where he/she has to navigate the instrument 24.

Figure 10:
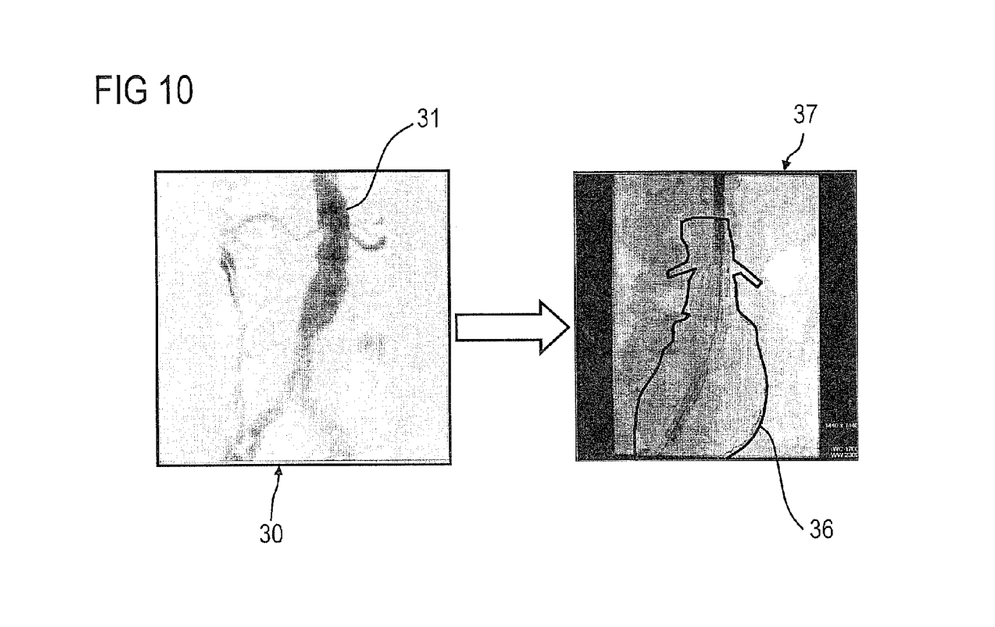
FIG. 10 shows a principle of a 2D/2D overlay.
Figure 11:
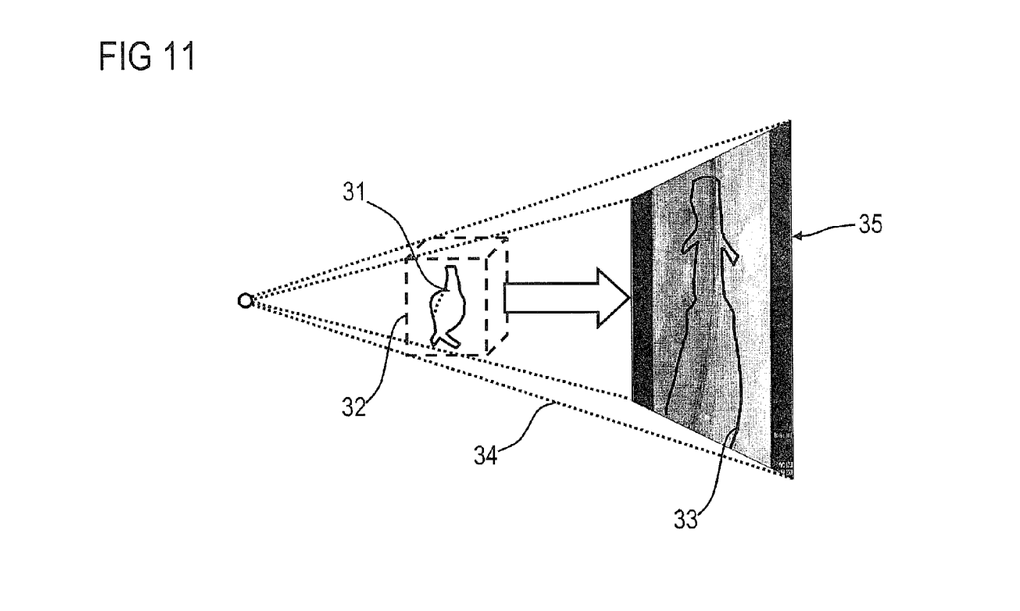
FIG. 11 shows a principle of a 2D/3D overlay.

The principle of the 2D/2D and 2D/3D overlay is now explained in more detail with the aid of FIGS. 10 and 11.

In order already nowadays to provide the physician with additional information when positioning the AAA stent, a previously recorded reference image is anatomically correctly overlaid onto the fluoroscopy image. This reference image may either be a 2D angiography 30 (DSA) of the abdominal aortic aneurysm 31 according to FIG. 10 or more expediently a 3D data record, for instance computed tomography, of the aortic aneurysm 31 according to FIG. 11, such as indicated symbolically.

In FIG. 11, a 3D segmentation of the aorta with the abdominal aortic aneurysm 31 from the pre-interventionally generated 3D data record was implemented as a prerequisite, which can be calculated for instance as a 3D grid model 32, such as is shown by way of example in the cube. The 3D grid model 32 is projected into the fluoroscopy image as segmentation 33, such as is symbolized by the dotted lines 34, and a 2D/3D overlay image 35 or reference image is obtained.

A pre-segmented, pre-operative computed tomography is used for instance for this 3D overlay. No additional contrast agent is therefore actually also needed here.

By contrast, in FIG. 10, there is no 3D grid model 32, but instead only the 2D angiography 30. The abdominal aortic aneurysm 31 in the 2D angiography 30 is segmented and this 2D segmentation 36 is projected into the fluoroscopy image (if also only precisely from this view) and a 2D/2D overlay image 37 or reference image is obtained.

For this 2D overlay by means of a DSA, a single contrast agent administration is however needed, the advantage of a "normal" roadmap is however that certain changes to the C-arm 2 such as zoom, SID and/or small couch movements can be included.

In the case of the two FIGS. 10 and 11, it is always only the outline of the 2D projection and not the full model which is shown.

Resulting from the 2D angiography 30 to the 2D overlay image 35 are the steps segmentation of the aorta with the abdominal aortic aneurysm 31 in the 2D angiography 30 and displaying the outlines of the segmented aorta as a 2D segmentation 36 in the native fluoroscopy image.

The main prerequisite for the inventive representation is an adaptive reference image registered to the C-arm, as is explained further with the aid of FIGS. 10 and 11, this may be either a 3D data record which is registered to the C-arm, for instance a previously implemented CT angiography or a C-arm CT recorded during the intervention or a 2D reference image registered to the C-arm (for instance a DSA), which adjusts to the different zoom, SID, couch settings etc.

(see DE 10 2008 023 918 A1)

SID=Source Image Distance/x-ray emitter-x-ray detector distance

To simplify matters, the principle of the inventive generation of virtual roadmap mask images is described below with the aid of an aortic aneurysm. Further exemplary embodiments or examples of use are found below.

The 3D data record registered to the C-arm is expediently pre-segmented. It is insignificant here how this happens, in other words whether the aorta was automatically segmented by means of a mathematical method or was "cut out" manually by means of a user for instance.

It is also insignificant for the inventive apparatus and the inventive method how this segmentation is represented, in other words for instance as a mask which displays the regions which do not belong the segmentation, as a surface grid, which spans the wall of the segmented aorta for instance or as a mathematical model, such as for instance an encoding of the centerlines and surfaces of the segmentation as a 2D spline or non-uniform rational B-spline (NURBS).

The aim of the inventive method is to generate a mask image for a roadmap without the renewed or repeated administration of contrast agent for changing angulations, couch positions etc. If this mask image is subtracted from the fluoroscopy live images such as with the conventional roadmap, then the usual roadmap representation is produced again. The subsequent description therefore concentrates on the generation of the mask image.

The registered and superimposed reference image, in this case in other words the 3D segmentation projected into the fluoroscopy image (see FIG. 12) is used for the generation of the reference image. Above all with segmented reference images, the precise projection of the vessel outline on the 2D image is known. The mask image 25 is now easily generated such that the image regions of the initial fluoroscopy image lying inside of the segmentation are "artificially" contrasted (FIG. 13). There are several options here. The pixel ranges within the vessel outline may for instance be simply set to black, be darkened by a specific "offset" (for instance 100 grayscale values in a 256 stage image), be "darkened" according to the local thickness of the vessels (known by the segmentation) or replaced, colored and/or darkened in accordance with a mathematical forward projection of the segmentation (DRR).

The result in all instances is a mask image 25, the subtraction of which from the fluoroscopy live images 23 once again results in the roadmap image shown in FIGS. 10 and 11, nevertheless without having to provide any contrast agent.

Figure 12:
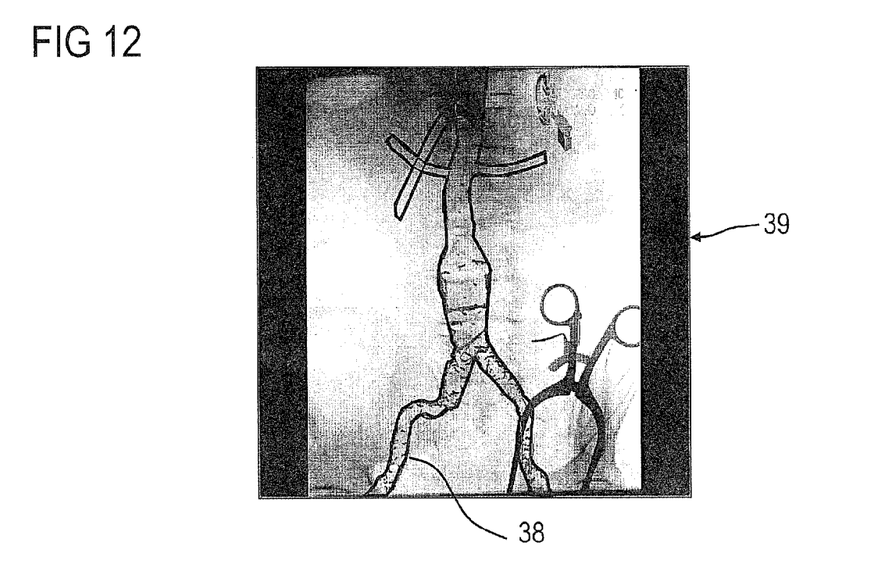
FIG. 12 shows a segmentation for a "virtual roadmap mask"
Figure 13:
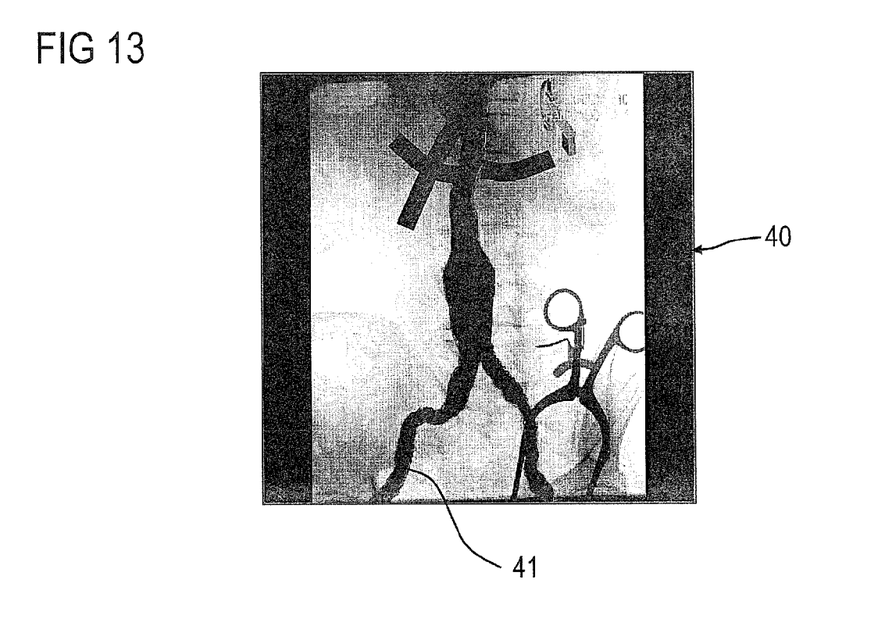
FIG. 13 shows a generation of a "virtual roadmap mask"

The principle behind generating a "virtual roadmap mask" is now explained in more detail on the basis of the 2D/3D and/or 2D/2D overlay with the aid of FIGS. 12 and 13.

A mask image for a roadmap is generated by the inventive apparatus without administering contrast agent, as is illustrated with the aid of FIGS. 12 and 13. One of the overlay images 35 or 37 is used here as a reference image. The aorta and aneurysm 38 are segmented from this since the precise projection of the vessel outline on the 2D image is above all known in the case of segmented reference images 39. A mask image 40 is now easily generated such that the image regions lying inside the segmentation of the aneurysm are artificially contrasted as a mask 41, in other words set to black, as apparent in FIG. 13.

A subtraction of this mask image once again produces the roadmap image shown in FIGS. 10 and 11, nevertheless without having to administer contrast agent.

While the contrasted vessels can only be shown in a planar fashion in "normal" mask images, additional information can be displayed in the "virtual" mask images 40.

Figure 14:
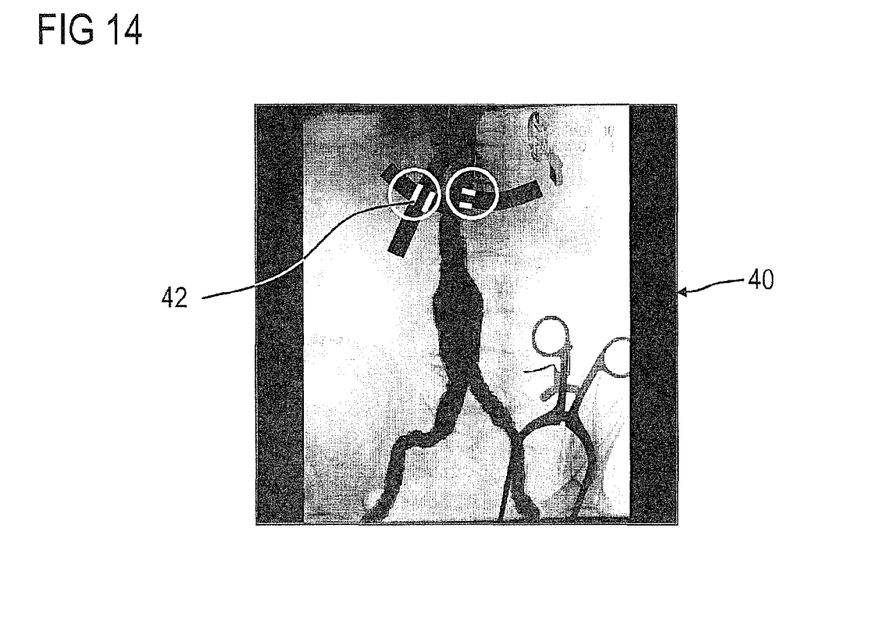
FIG. 14 shows a "virtual roadmap mask" with additional information.
Figure 19:
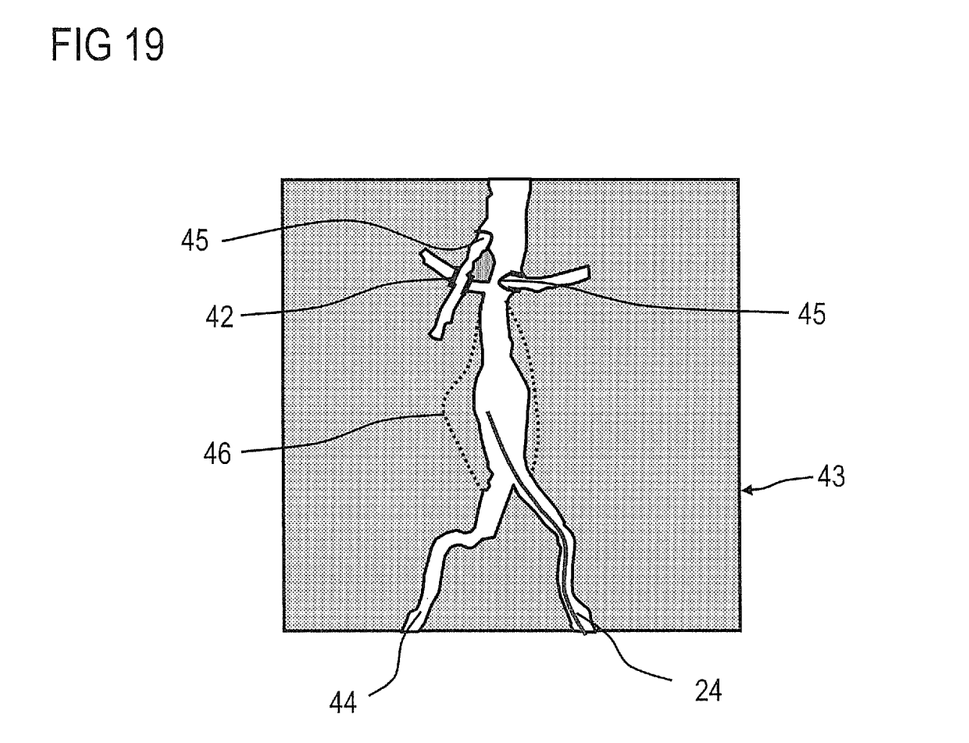
FIG. 19 shows an inventive roadmap having a plurality of additional information.

Therefore vascular occlusions 42 can be produced for instance in the mask 41 through recesses of the mask parts for instance, as shown with the aid of FIG. 14, so that a virtually plastic impression is produced. The vascular occlusions 42 are only marked by circles in the Figures for the purpose of demonstrating improved visibility. They do not need to be present in the mask image 40 as shown in FIG. 19.

Figure 15:
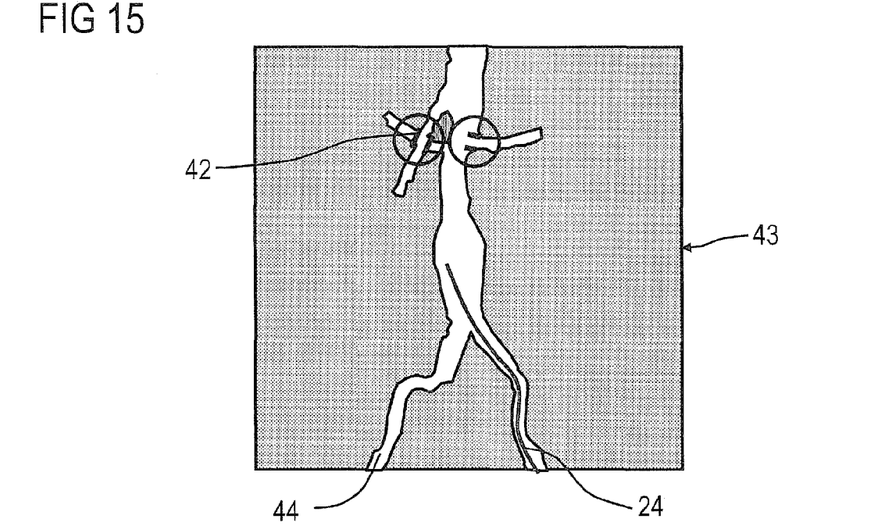
FIGS. 15 and 16 show roadmaps with additional information.

In the corresponding roadmap image 43 shown in FIG. 15, the vessel courses 44 are then clearly apparent, which significantly simplifies the navigation of the instrument 24 for instance.

Furthermore, orifices 45 can be produced in the mask 41 for instance (simply through recesses of mask parts). In the associated roadmap image 43, the orifices 45 are then clearly visible, as a result of which the navigation is noticeably simplified, as is shown clearly with the aid of FIG. 16. The orifices 45 are likewise marked by circles for better visibility in the Figure.

Figure 17:
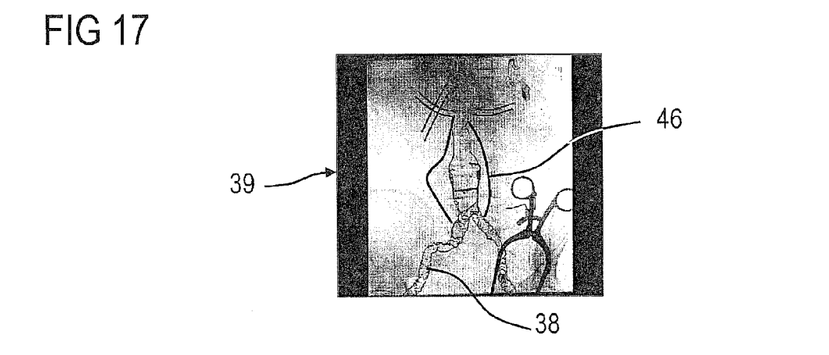
FIG. 17 shows a segmentation for a "virtual roadmap mask"
Figure 18:
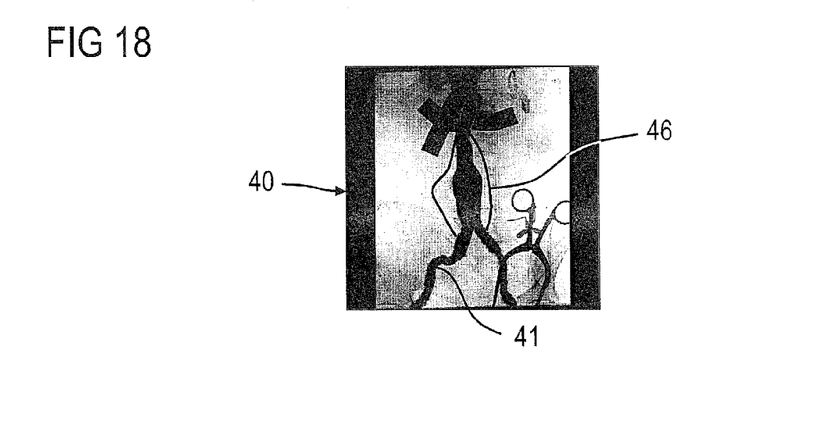
FIG. 18 shows a generation of a "virtual roadmap mask"

A thrombus can be highlighted in the "virtual roadmap mask" for instance as further additional information. FIG. 17 shows how a thrombus 46 is displayed in the segmented reference image 39. This segmented thrombus 46 is then clearly visible in the corresponding roadmap image 40 according to FIG. 18, which significantly simplifies the navigation.

In FIG. 19, the completely inventive mask image 43 is then reproduced with the additional information relating to the vascular courses 44, vascular occlusions 42, orifices 45 and the segmented thrombus 46. The instrument 24 can then be reliably navigated for instance in the clearly visible vascular courses 44.

By means of the inventive apparatus and the inventive method, the physician is provided with the roadmap representation to which he/she is accustomed for a complex intervention, without contrast agent having to be repeatedly injected for instance during angulations changes.

The present invention proposes the generation of mask images from the overlaid reference images, so that the physician is able to keep his/her familiar roadmap representation (also from any angulations) without repeatedly administering contrast agents.

Furthermore, this "virtual" roadmap representation enables the introduction of additional information, which cannot be reproduced in "normal" roadmap representations.

In other embodiments and/or extensions, additional information can also be inventively encoded in this "virtual" roadmap, which does not offer a normal roadmap representation.

Anatomical Reference:

On account of the segmentation information, the mask image can be configured such that following subtraction, the regions outside of the aorta are not "subtracted", but are instead also represented. This is thus advantageous in that the roadmap representation applies within the aorta, while outside thereof the complete anatomical reference with vertebrae, pelvis, bowel etc. is visible.

Vessel coverages (FIGS. 14 and 15):

While in "normal" mask images, the contrasted vessels can only be shown 2-dimensionally, more information can be shown in the "virtual". Thus vascular occlusions can therefore be produced in the mask for instance (simply through recesses of mask parts) (FIG. 14). In the corresponding roadmap image (FIG. 15), the vessel courses are then clearly apparent which significantly simplifies the navigation.

Figure 16:
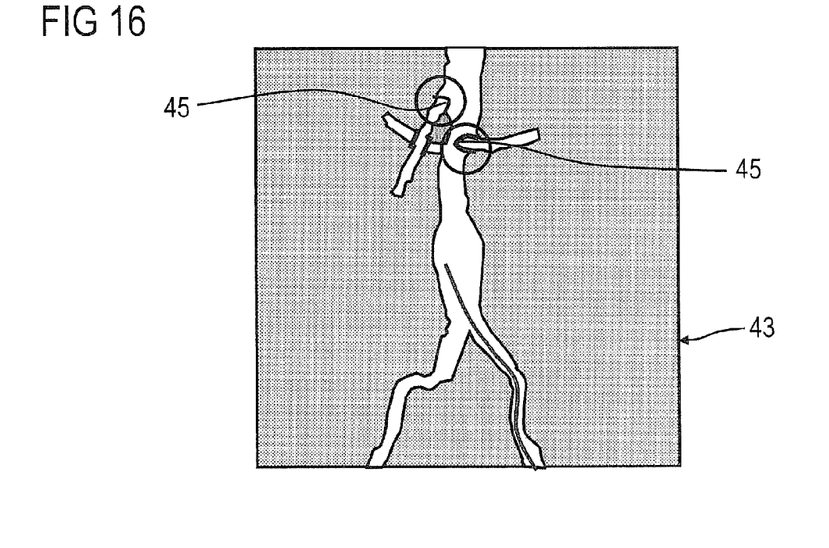

Vessel outlets (orifices, FIG. 16):

Vessel outlets or orifices can also be produced in the mask for instance. In the corresponding roadmap image, the orifices are then clearly apparent, which significantly simplifies navigation.

Further additional information, for instance aorta thrombus (FIG. 19):

Whereas in "normal" mask images only the actually contrasted vessels can be shown, in the "virtual" mask image, additional information can also be shown. If a segmentation of a thrombus exists for instance, then the corresponding outline can be produced in the mask (FIG. 17). In the corresponding roadmap image (FIG. 18), the thrombus course is then clearly apparent which can significantly simplify the navigation and positioning of a stent.

The method can in principle be extended to all procedures, which profit from the overlay of (presegmented) reference images, and in which the roadmap technology is used for representation purposes, these are for instance
- the exchange of aortic valves,
- interventions in neuroradiology,
- interventions in the periphery (arms, legs) and
- interventions in the thoracic aorta.

The "roadmap" representation in the angiography in principle refers to the following procedure:
- A: creating a 2D mask image WITH contrast agent (shows vascular system and anatomical background)
- B: recording live images WITHOUT contrast agent, but possibly with instruments (shows this instrument and the anatomical background)
- Representation as a subtraction image B–A, ONLY shows the contrasted vascular system and the instrument, the anatomical background is subtracted.

Alternatively, the mask image can also be recorded without contrast agent, then only the instrument, and not the vascular system are shown in the subtraction image, which is therefore not desirable.

The DISADVANTAGES of this known method are:

If the C-arm 2 moves, the mask image A no longer passes to the live image B and the technology cannot be used and/or a new mask image A must be created.

The inventive approach (as an example with a segmented 3D volume) is:
- with a volume registered to the C-arm 2, which indicates the vascular system, the volume can be anatomically correctly displayed into a 2D image recorded by the C-arm 2 for all angulations of the C-arm 2 etc.
- then a mask image A1 is created WITHOUT contrast agent, on which the vascular system is NEVERTHELESS visible, in which the 3D display of the vessel on the 2D image A1 is to be colored black accordingly as a "virtual contrast".
- live images are then recorded again and B–A1 is shown as a roadmap with vessels, without having administered contrast agent.

Advantage:

This process can be repeated any number of times without having provided contrast means each time. With each new angulation, the first image with the displayed vessels is easily used as a mask and is detached from the rest.

What is claimed is:

1. An angiography system for an angiographic examination on an examination object of a patient, comprising:
    an x-ray emitter attached to an end of a C-arm;
    an x-ray detector attached to another end of the C-arm;
    a patient support couch for supporting the patient;
    a system control unit; and
    a monitor,
    wherein the system control unit is configured to:
        obtain a reference image that is adjusted to a current geometric setting of the C-arm,
        register the reference image the current geometric setting of the C-arm,
        segment the examination object in the reference image if necessary,
        generate a mask image from the reference image with image regions lying within the segmentation being artificially contrasted without administrating contrast agent,
        subtract the mask image from fluoroscopy live images acquired by the angiography system, and
        generate a roadmap image from the subtraction, and
    wherein the roadmap image is displayed on the monitor.

2. The angiography system as claimed in claim 1, wherein the image regions lying within the segmentation are contrasted by being set to black.

3. The angiography system as claimed in claim 1, wherein the image regions lying within the segmentation are contrasted by being darkened with a specific offset value.

4. The angiography system as claimed in claim 1, wherein the image regions lying with the segmentation are contrasted by being darkened according to a local thickness of a vessel.

5. The angiography system as claimed in claim 4, wherein the local thickness of the vessel is calculated from distances of edges of the vessel in the segmentation.

6. The angiography system as claimed in claim 1, wherein the image regions lying within the segmentation are contrasted by being homogenously colored.

7. The angiography system as claimed in claim 1, wherein the image regions lying within the segmentation are contrasted by a mathematical forward projection of the segmentation.

8. The angiography system as claimed in claim 1, wherein the reference image is a 2D image and is adjusted to different geometric settings of the angiography system.

9. The angiography system as claimed in claim 8, wherein the different geometric settings comprise changes to a zoom, a Source Image Distance, and/or couch settings.

10. The angiography system as claimed in claim 1, wherein the reference image is a 3D data record of a CT angiography implemented prior to an intervention or a C-arm CT angiography recorded during the intervention.

11. The angiography system as claimed in claim 1, wherein the system control unit effects a display of additional information in the mask image and/or the roadmap image.

12. The angiography system as claimed in claim 11, wherein the additional information is displayed through recesses of mask parts in the mask image and/or the roadmap image.

13. The angiography system as claimed in claim 11, wherein the additional information comprises vascular courses, vascular occlusions, orifices and/or thrombi.

14. An angiographic examination method for an angiographic examination on an examination object of a patient, comprising:

detecting a reference image by an angiography system having a C-arm, wherein the reference image is adjusted to a current geometric setting of the C-arm;
registering the reference image to the current geometric setting of the C-arm by a system control unit;
segmenting the examination object in the reference image if necessary by the system control unit;
creating a mask image from the reference image by the system control unit for different alignments of the C-arm with image regions lying within the segmentation being artificially contrasted without administering contrast agent;
generating fluoroscopy live images by the angiography system;
subtracting the mask image from the fluoroscopy live images by the system control unit;
generating a roadmap image by the system control unit from the subtraction; and
displaying the roadmap image on a monitor.

15. The angiographic examination method as claimed in claim 14, wherein the mask image is created with image regions lying within the segmentation being contrasted.

16. The angiographic examination method as claimed in claim 15, wherein the image regions lying within the segmentation are contrasted by being set to black or darkened according to a local thickness of the vessel.

17. The angiographic examination method as claimed in claim 14, wherein an aneurysm of the patient is segmented.

18. The angiographic examination method as claimed in claim 14, wherein additional information is superimposed into the mask image and/or the road map image.

19. The angiographic examination method as claimed in claim 18, wherein the additional information is displayed through recesses of mask parts in the mask image and/or the road map image.

20. The angiographic examination method as claimed in claim 18, wherein the additional information comprises vascular courses, vascular occlusions, orifices and/or thrombi.

* * * * *